(12) United States Patent
Klecha (10) Patent No.: US 9,779,922 B1
(45) Date of Patent: Oct. 3, 2017

(54) GENERATION OF DISCOVERY ION CURRENTS AND MASS SPECTROMETRY AND USES THEREOF

(71) Applicant: Advion Inc., Ithaca, NY (US)

(72) Inventor: Lawrence Klecha, Ithaca, NY (US)

(73) Assignee: Advion Inc., Ithaca, NY (US)

( * ) Notice: Subject to any disclaimer, the term of this patent is extended or adjusted under 35 U.S.C. 154(b) by 0 days.

(21) Appl. No.: 15/408,146

(22) Filed: Jan. 17, 2017

(51) Int. Cl.
*H01J 49/00* (2006.01)
*H01J 49/04* (2006.01)

(52) U.S. Cl.
CPC ...... *H01J 49/0031* (2013.01); *H01J 49/0431* (2013.01)

(58) Field of Classification Search
CPC .... H01J 49/0431; H01J 49/0031; H01J 49/02; G01N 30/82; G01N 30/10; G01N 30/62; G01N 30/80; G01N 30/84; G01N 30/7233
See application file for complete search history.

(56) References Cited

U.S. PATENT DOCUMENTS

| | | | | |
|---|---|---|---|---|
| 6,106,710 A | * | 8/2000 | Fischer | G01N 30/82 210/143 |
| 2003/0124606 A1 | * | 7/2003 | Suckau | G01N 33/6818 435/7.23 |
| 2009/0294645 A1 | * | 12/2009 | Gorenstein | G06F 19/703 250/282 |
| 2010/0237235 A1 | * | 9/2010 | Ozbal | G01N 30/24 250/282 |
| 2014/0284279 A1 | * | 9/2014 | Warngren | G01N 30/72 210/659 |
| 2014/0312216 A1 | * | 10/2014 | Prosser | G01N 30/724 250/282 |

* cited by examiner

*Primary Examiner* — Wyatt Stoffa
(74) *Attorney, Agent, or Firm* — Fish & Richardson P.C.

(57) ABSTRACT

Systems for the generation of discovery ion currents. One of the systems includes a mass spectrometer providing ion current measurement. The system includes a controller coupled to the mass spectrometer. The system also includes a liquid handler coupled to the controller and the mass spectrometer. The controller is configured to identify a base average ion current of each mass to charge interval, the mass to charge interval comprising at least one mass to charge channel. The controller is configured to calculate a relative change between a current ion current measurement for a charge interval to the base average for the charge interval. The controller is configured to compare the relative change to a threshold. The controller is also configured to, in response to determining that the relative change exceeds the threshold, start fraction collection using the liquid handler.

14 Claims, 9 Drawing Sheets

GENERATION OF DISCOVERY ION CURRENTS AND MASS SPECTROMETRY AND USES THEREOF

BACKGROUND

Mass spectrometry is an analytical technique that ionizes chemical species and sorts the ions based on their mass to charge ratio. Mass spectrometry is used in many different fields and is applied to pure samples as well as complex mixtures.

In general, a mass spectrum is a plot of the ion signal intensity as a function of the mass-to-charge ratio. These spectra are used to determine the elemental or isotopic signature of a sample, the masses of particles and of molecules, and to elucidate the chemical structures of molecules, such as peptides and other chemical compounds.

SUMMARY

This disclosure generally relates to the field of mass spectrometers and more particularly to systems analyzing a flow of unknown compounds in liquid, vapor, or gaseous form towards the mass spectrometer analysis system.

In one implementation, a system includes a mass spectrometer, the mass spectrometer providing ion current measurement for a plurality of mass to charge channels over a period of time. The system includes a controller coupled to the mass spectrometer. The system also includes a liquid handler coupled to the controller and the mass spectrometer. The controller is configured to identify a base average ion current of each mass to charge interval, the mass to charge interval comprising at least one mass to charge channel. The controller is also configured to calculate a relative change between a current ion current measurement for a charge interval to the base average for the charge interval. The controller is also configured to compare the relative change to a threshold. The system is also configured such that in response to determining that the relative change exceeds the threshold, the controller sends a control signal to the liquid handler.

In another implementation, a system includes a mass spectrometer, the mass spectrometer providing ion current measurement for a plurality of mass to charge channels over a period of time. The system includes a controller coupled to the mass spectrometer. The system also includes a liquid handler coupled to the controller and the mass spectrometer. The controller is configured to identify a base average ion current of each mass to charge interval, the mass to charge interval comprising at least one mass to charge channel. The controller is also configured to calculate a relative change between a current ion current measurement for a charge interval to the base average for the charge interval. The controller is also configured to calculate a sum of the relative changes for each charge interval in the scan. The controller is also configured to compare the sum of relative changes to a threshold. The controller is also configured such that in response to determining that the sum of relative changes exceeds the threshold, the controller sends a control signal to the liquid handler.

The system may also include one or more of the following features, alone or in combination. The controller may be further configured to plot the sum of relative changes for each charge interval of a scan vs. the time of the scan. The controller may be configured to identify a base average ion current of each mass to charge interval, the mass to charge interval comprising at least one mass to charge channel, calculate a relative change between a current ion current measurement for a charge interval to the base average for the charge interval, calculate a sum of the relative changes for each charge interval in the scan, compare the sum of relative changes to a threshold; and in response to determining that the sum of relative changes exceeds the threshold, start fraction collection using a fraction collector. The controller may be configured to apply algorithmic smoothing to the ion current measurements in a scan of mass to charge channels. The controller may be configured to apply algorithmic smoothing to the relative changes in a scan of mass to charge channels. The liquid handler may be a fraction collector. The control signal may cause the fraction collector to start fraction collection.

Particular embodiments of the subject matter described in this specification can be implemented so as to realize one or more of the following advantages. Fractional material collecting may be improved, Control signals can be generated based on a mass spectrometry analysis of an unknown sample, and data analysis/visualization can be improved.

The details of one or more embodiments of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
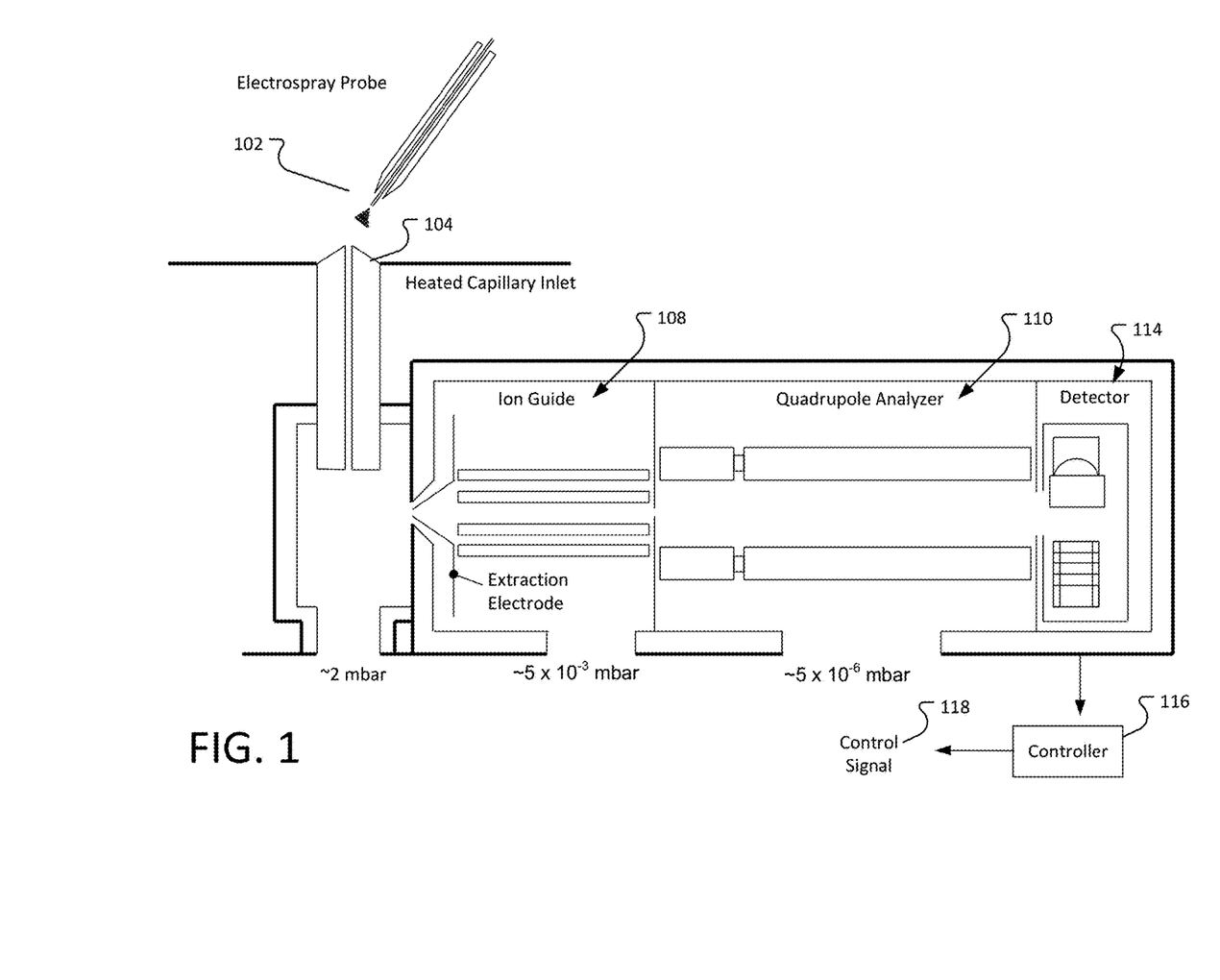
FIG. 1 illustrates an exemplary environment in which a control signal can be generated based on mass spectrometry.

FIG. 1 illustrates an exemplary environment in which a control signal can be generated based on mass spectrometry analysis of an unknown sample. A sample (represented by the electrospray probe 102) is provided to through a heated capillary inlet 104 to a vaporization and/or ionization area. The vaporization and/or ionization area vaporizes the sample and ionizes the particles of the vaporized sample. The ionized elements and molecules can be passed through an ion guide (e.g. a quadpole, hexapole, octopole, etc.) area 108 as an ion beam. In general the hexapole area (or bridge) can be used to focus the ion beam, so that it leaves the hexapole area as a narrow beam.

Within the quadrapole analyzer 110, the ionized sample is subjected to electric fields that can deflect the ionized sample along different paths.

The degree to which the ionized samples are deflected is a function of the mass of the ions and charge of the ions. Only ions with the proper mass to charge ratio reach the detector 114 are detected. Altering the electric fields, changes which mass to charge ratio will have the desired or stable trajectory, and different ions can reach the detector 114. Generally, a mass spectrometer will cycle through different mass to charge channels.

A controller 116 can receive the information from the detector 114 (or from the mass spectrometer, which obtains information from the detector 114) and, coupled with information about the electric field, can make determinations about the characteristics of the sample and send out a control signal 118 in response to those determinations.

Generally, the control signals 118 can be determined from any of a flow of unknown compounds in liquid, vapor, or gaseous form towards the mass spectrometer analysis system, (e.g., flow injection analysis (FIA) mass spectrometry, volatile atmospheric pressure chemical ionization (vAPCI) mass spectrometry or chromatography such as reverse phase high performance liquid chromatography (RP-HPLC) mass spectrometry, flash to chromatography mass spectrometry or ion chromatography mass spectrometry). Each of these systems can be characterized by the separation of the analytes and matrix in the time domain and results in a sequential delivery of compounds to the ion source of the mass spectrometry system over the analysis time either not separated, partially separated or baseline separated.

The control signal 118 can be used to control downstream hardware components, such as a liquid handler (e.g., a fraction collector, fragmentation device), change mass spectrometer settings during the analysis run (resulting in e.g. fragmentation) or changes to the data output.

The controller 116 can also be used for post-acquisition data processing and can guide data analysis via automatic data marking and labeling to improve mass spectrometry data visualization.

Figure 2:
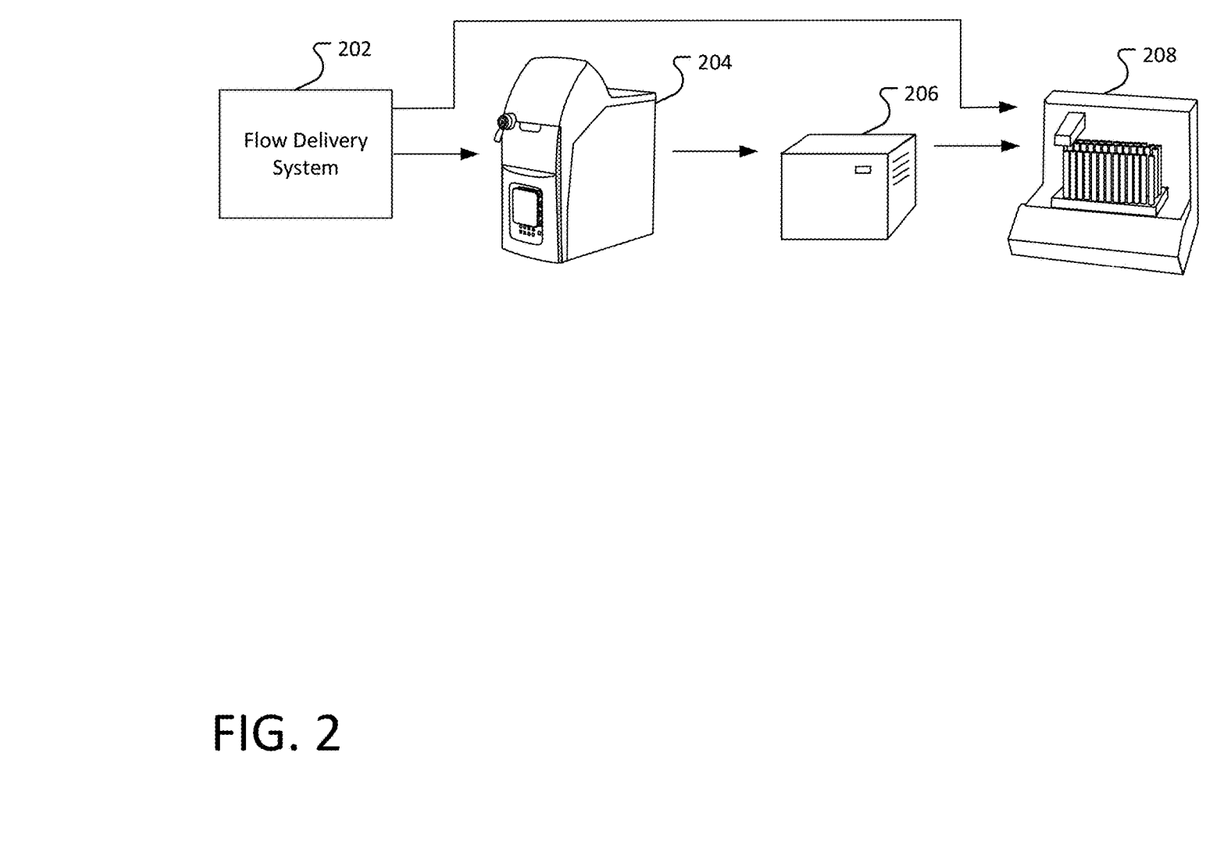
FIG. 2 illustrates a system that uses mass spectrometry to control downstream processes.

FIG. 2 illustrates a system that uses mass spectrometry to control downstream processes. Mass spectrometers 204 can be coupled with flow delivery systems 202 in order to transport analyte containing samples to the ion generating source of the mass spectrometer 204. After ionization, the mass spectrometer analyzer separates the generated ions by their mass to charge ratio and the mass spectrometry detector system provides the ion current signal dependent on the m/z (mass-to-charge) ratio. Data processing then allows to identify, characterize, and quantitate the analytes of interest from the sample.

The flow delivery systems 202 can include methods such as volatile atmospheric chemical ionization (vAPCI), which is characterized by analytes in a gaseous or vapor phase delivered to the mass spectrometer en-block, flow injection analysis (FIA) which is characterized by analytes delivered towards the ion source of an MS system en-block but in a solvent stream or workflows that additionally include chromatographic separation material such as reverse phase HPLC, flash chromatography, ion chromatography and so on, all additionally characterized by the separation (or partial separation) of analytes and matrix in the time domain and a sequential delivery to the ion source of the MS system.

In many workflows, the mass spectrometer 204 is only analyzing part of the effluent from the flow stream with a majority or minority portion of the flow being used for further downstream processing, such as an additional detector system or for physical collection of the flow in separate fractions (downstream hardware components). In those set-ups, the mass spectrometry detector signal can be used by a controller 206 to control the downstream fraction collection 208 for automated collection and processing of unknown analytes in samples.

The controller 206 can accept signals from the mass spectrometer 204 and trigger downstream processes based on the signal, as discussed further below. In some implementations, the controller 206 may be integrated with the mass spectrometer 204 or the downstream component (such as the liquid handler 208). In some implementations, the controller may be a standalone hardware component or a computer coupled to the mass spectrometer 204 and the downstream component. In some implementations, the sample is directed to the down steam component directly from the flow delivery system 202. The downstream component receives a signals from the controller to indicate actions performed on the sample. The flow delivery system 202 may coordinate the flow between the mass spectrometer/controller and the downstream component to cause the control signal sent to the downstream component to coincide with flow from the flow delivery system to the downstream component.

Triggering the downstream external device, for example a liquid handler 208, is challenging since the mass spectrometer 204 provides many channels of ion current data and the mass-to-charge ratio (channel) of an analyte of interest is usually not known prior to analysis. Further, the analyte mass-to-charge ion current signal detected is usually small compared to other background or contaminant ion current signals (for example, from solvents, ambient air or other contaminants) and the ion current signal behavior over time can take various forms such as block, Gaussian, Gaussian tailing, Gaussian fronting etc.

Figure 3A:
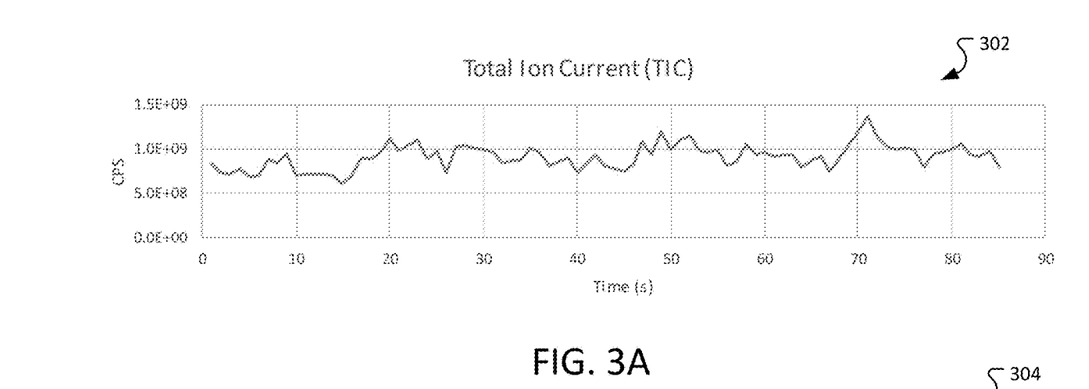
FIG. 3A-C are graphs of a flow injection analysis of Benzoic acid in a solvent flow.
Figure 3B:
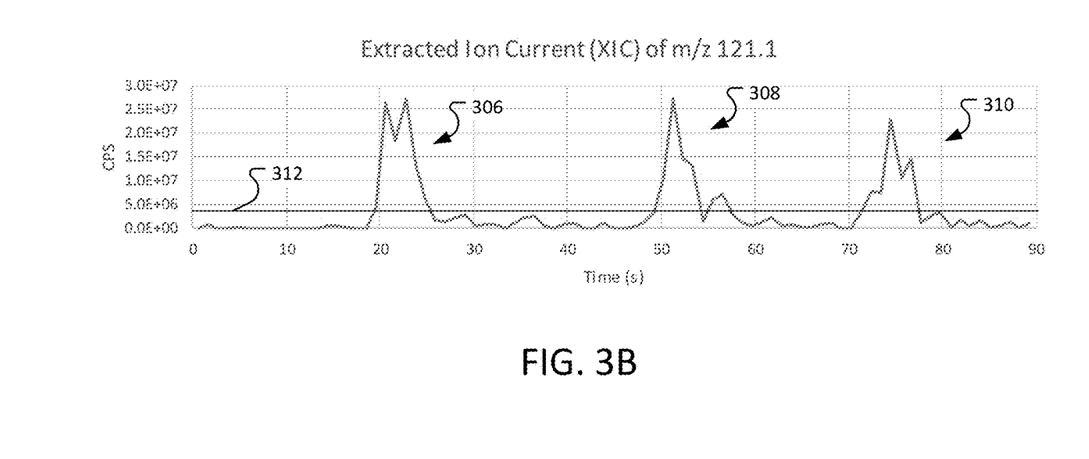
Figure 3C:
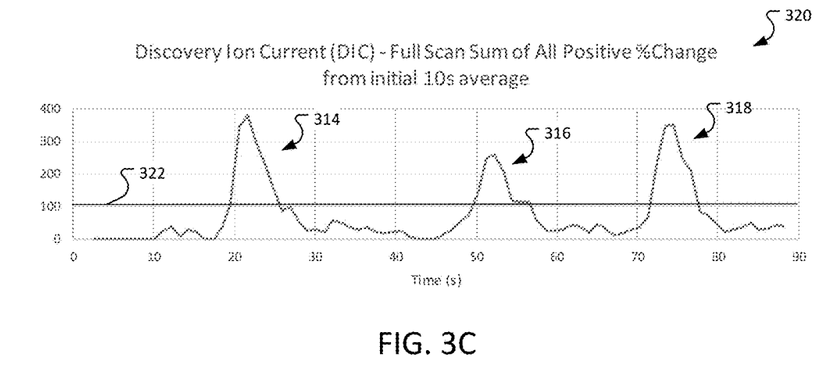

FIG. 3A-C are graphs of a flow injection analysis of benzoic acid in a solvent flow of 200 µL/min acetonitrile with 0.1% acetic acid. 5 µL injections of 10 ng/µL dissolved in acetonitrile were injected three times within a 90 sec time frame and the mass spectrometer was set to scan m/z 10-2000 in negative ion mode for a scan time of 500 ms.

As used herein a scan refers to a cycle of the mass spectrometer measurements across all mass to charge intervals (for example, a scan from 10-2000 m/z). A mass spectrometer may perform one or more scans on a sample.

FIG. 3A is a graph 302 showing the resulting total ion current (TIC). The current values of all signal intensities in all channels are summed and plotted against time. The graph 302 illustrates one challenge with controlling downstream systems based on mass spectrometry. Even a comparatively high current signal for an analyte can get drowned out by the intensity, multitude, and random fluctuations of background ion currents in different channels and at different m/z values. As a result, (as shown in the graph) no discernable peak with useful signal to noise is visible or can be utilized to make trigger decisions.

FIG. 3B is a graph 304 of the extracted ion current (XIC) of the known analyte Benzoic acid with an m/z of 121.1 for the (M—H)— de-protonated molecule. The line 312 simulates a potential trigger criteria for downstream components. MS signal from the three injections into the solvent stream is now clearly visible (as peaks 306, 308, and 310). The extracted ion current provides a better graphical representation of the sample and allows for the definition of threshold levels to trigger further events (for example, peaks 306, 308, 310). However, the extracted ion current is only measurable for a particular m/z interval. As such, the extracted ion current requires prior knowledge of the m/z interval of the analyte of interest and knowledge about the ionization preference of the analyte in question under the ionization conditions of the MS set-up (for example, knowledge of the analyte, its formation of salt adducts, the charge state of the ion formed, polarity etc.). As such, the extraction ion current is of limited use in practical applications.

FIG. 3C is a graph 320 of the discovery ion current (DIC) which allows triggering downstream systems without prior knowledge of the m/z ratio. The Discovery Ion Current (DIC) provides a current signal similar to an XIC or TIC, without the need for prior knowledge of the analytes and with a significantly improved signal-to-noise ratio.

The DIC presents the highest ion signal rate change over the entire m/z scan and from contributors of any of the m/z channels (including multiple contributors due to salt adducts or multiple charged species). The DIC allows threshold definitions (represented by the line 322) to trigger downstream components (for example, peaks 314, 316, and 318) or change current MS parameters or additionally visualize m/z contributors.

Post processing, the DIC allows user guidance to further analyze data in certain time points of the analysis compared to other times.

The DIC can be computed using either a fixed point relative change sum or a rolling relative change sum. The fixed point relative change sum works best with an analysis that is characterized by a near constant background signal in each scan for the entirety of the analysis run (e.g. FIA-MS, vAPCI-MS, Flash-MS with part of the flow directed towards the MS). The rolling relative change DIC may be used, for example, for analysis methods that are characterized by a slow change of the background ion current signal (for example, RP-HPLC-MS, GC-MS or ion chromatography mass spectrometry) caused by changes in flow rate, solvent flow composition or temperature over the time of the analysis.

The fixed point change in sum can be determined, for example, using some number (1 to x) of mass spectrometry scans prior to the analysis run start or at the beginning of the analysis. In general, one mass spectrometry scan includes the ion current measurement within a set time frame (scan time) and for a set number of m/z intervals (bins or channels) to cover the selected mass-to-charge ratio (for example: 500 ms per scan, 10-2000 m/z range, 0.05 m/z per channel results in 39,800 channels with an ion current signal each). These scans may sweep the positive Ion m/z range, negative ion m/z range, or both concurrently.

The controller may determine the average ion current of each m/z channel (or larger group of bins of m/z channels to lighten the processing/memory load referred to as an m/z interval) within the selected number of scans (1 to x).

For each following scan of the analysis run, the controller may calculate the relative change (percent change, percent difference or first derivative) from the actual scan versus the initial average for each m/z interval, bin, or channel (in some implementations, filtering options may be used pre- or post-calculation to reduce influence of random noise spikes, for example, n=3 scan median, box filter or other algorithmic filtering).

The controller may sum up all relative change values in the scan or just sum those values above a certain threshold (for example. sum only those m/z channels or bins with greater than a two times increase from the pre-scan average).

The controller may plot the sum for each scan versus time of the scan to generate a discovery ion current.

If any relative change value, either from single channels or for the sum of all values or in x number of successive scans are above or below a selected threshold a trigger signal can be used to control downstream hardware components or change software or hardware operating parameters of the mass spectrometry system or change the graphical output of the displayed data (for example, by placing a flag mark on the time scale or show the actual m/z value that was above or below the threshold.)

Figure 4A:
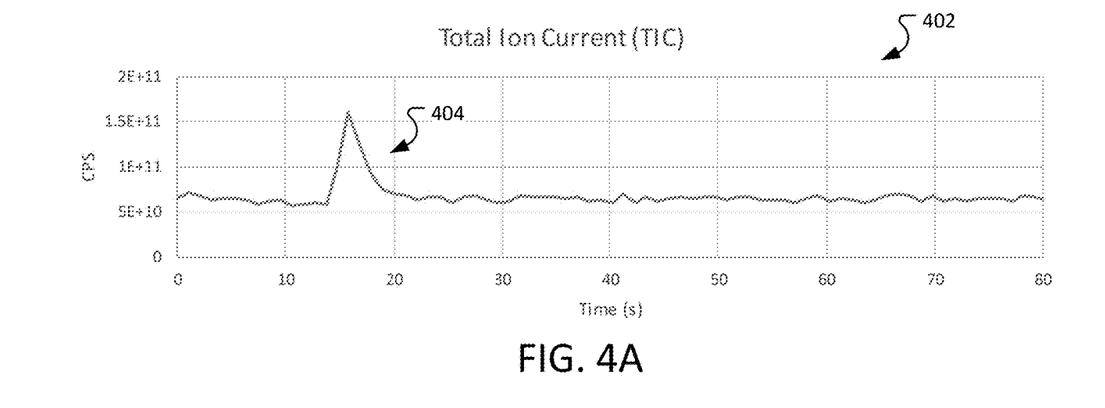
FIG. 4A-B are flow injection analysis of Ethyl 7-[1-(4-fluorophenyl)-4-isopropyl-2-phenyl-1H-imidazol-5-yl]-5-hydroxy-3-oxo-trans-6-heptenoate in a solvent flow.
Figure 4B:
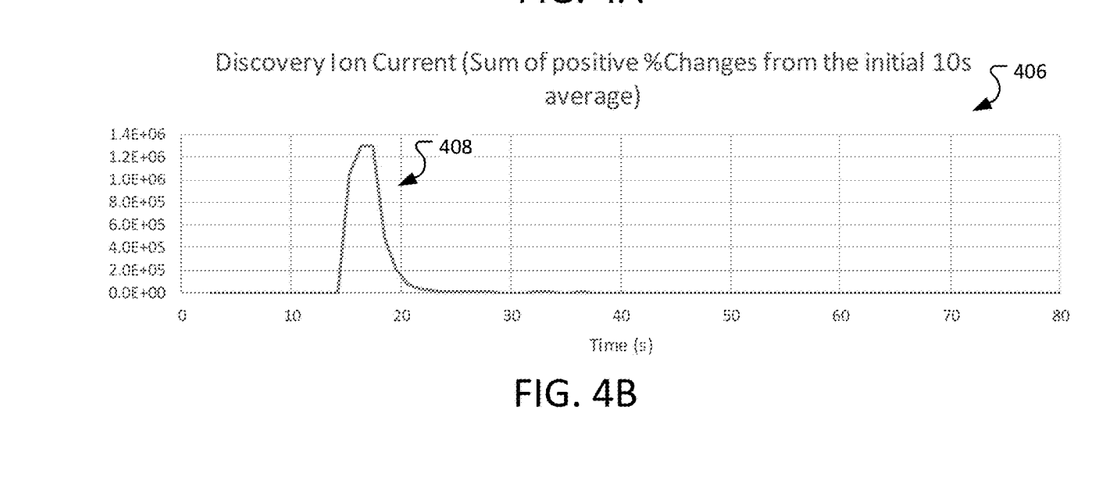

FIG. 4A-B are flow injection analysis of Ethyl 7-[1-(4-fluorophenyl)-4-isopropyl-2-phenyl-1H-imidazol-5-yl]-5-hydroxy-3-oxo-trans-6-heptenoate in a solvent flow of 500 µL/min 90/10 Acetonitrile/Water with 0.5% formic acid. 5 µL of 20 ng/µL dissolved in acetonitrile was injected once within an 80 sec time frame and the mass spectrometer was set to scan m/z 10-2000 both positive and negative mode for a scan time of 500 ms.

FIG. 4A is a graph 402 showing the resulting total ion current. A plot of all signal intensities in all the channels summed up and plotted against time, a small signal change 404 ($<1e^1$) is visible in the time range from 14-20 sec.

FIG. 4B is a graph 406 showing the discovery ion current (DIC) with a significant ion signal rate change ($>1e^6$) 408 in the 14-20 sec time frame. Signal-to-noise ratio in this plot enables simple identification of analyte elution time and would allow for easy trigger decisions. Again, no prior knowledge of the analyte m/z or polarity is required.

In some implementations the system can analyze either a negative ion polarity or a positive ion polarity without prior knowledge of the ion polarity.

Figure 5:
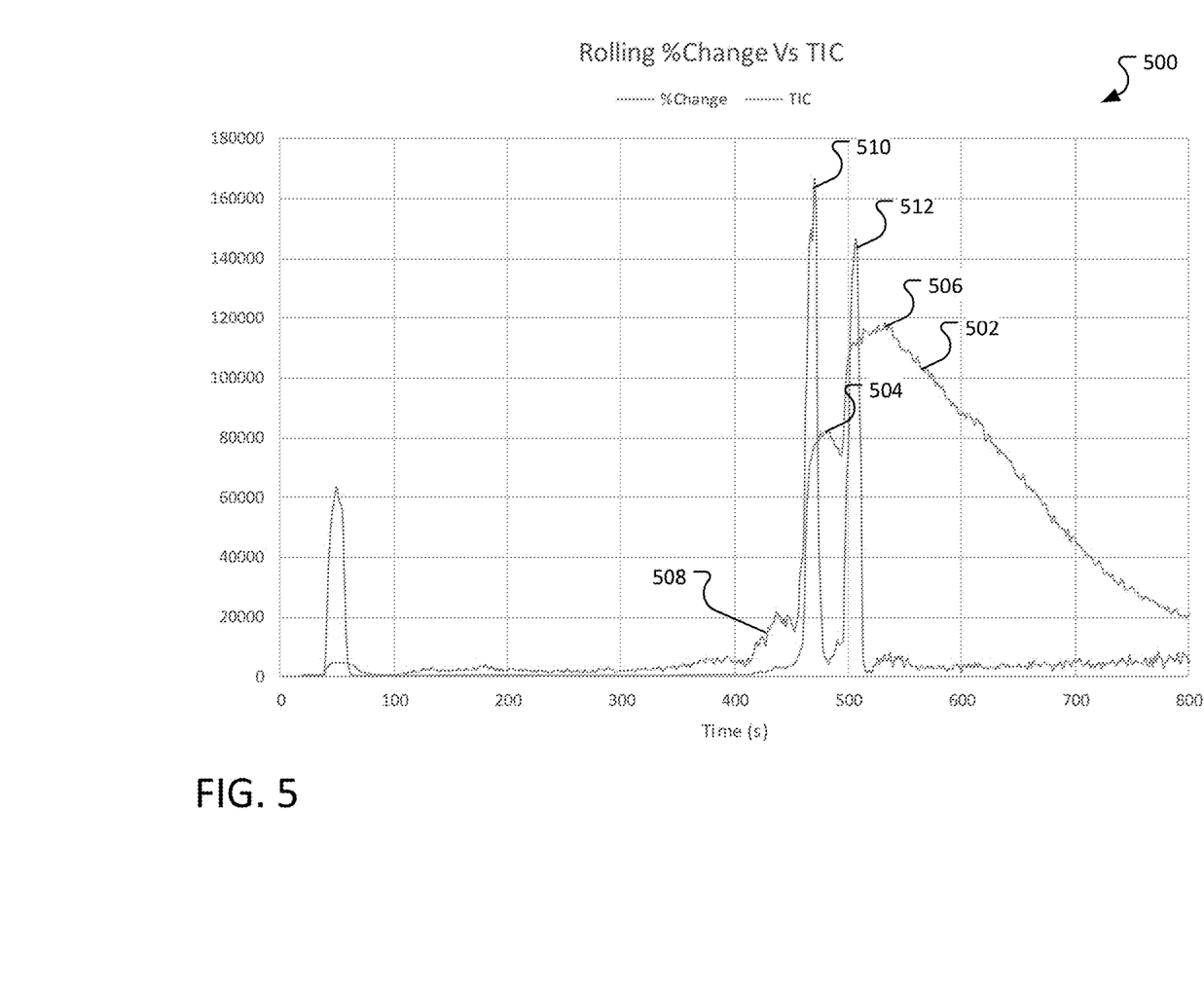
FIG. 5 is a graph of a RP-HPLC-MS analysis of a reduced human antibody using a gradient solvent flow from 10% organic to 100% organic over 800 seconds.

The DIC can also be calculated using a rolling point relative change sum. In this case the DIC created will show a spike (peak) for each new analyte that is passing into the MS detector (e.g., eluting from a chromatographic separation). For example, FIG. 5 is a graph 500 of a RP-HPLC-MS analysis of a reduced human antibody using a gradient solvent flow from 10% organic to 100% organic over 800 seconds. Antibody light chain is eluting slightly earlier than the antibody heavy chains during this rapid gradient run. The TIC line 502 shows the resulting total ion current (TIC), a plot of all signal intensities in all the channels summed up and plotted against time. Two very strong signals are visible at ca 480 (point 504) and 520 seconds (point 506) with significant tailing of at least the second signal, however it is unclear where the second signal starts since chromatographic separation is only partial. The rolling change line 508 shows the discovery ion current (DIC) with two strong signals at the respective left flank of the two peaks eluting form the RP-HPLC system (points 510 and 512). Here, the rolling DIC is able to indicate the beginning of the elution of the second peak and trigger either external processes or guide online MS hardware settings or post acquisition data analysis. Again, no prior knowledge of the sample composition is required to indicate at least two major components of the sample.

Using the rolling point DIC provides a sufficient ion current signal to make threshold decisions to trigger downstream hardware components, to trigger the stop of the current fraction collection for component one and force a new fraction collection in order to enhance the purity of both the previously collected analyte one as well as increase the total amount of collected component two in the second collection vial—regardless if the first analyte is still detected.

In some implementations, a stop trigger could be set up by fixed time, an indication by the rolling relative change DIC to go to a next vial, a fixed relative change DIC, the XIC determined by the algorithm of the rolling relative change DIC, or the end of the analysis run.

Rolling relative change DIC can indicate the start of a new analyte eluting from separation media for poorly separated peaks, both on-line or post processing for further guided data analysis.

Figure 6A:
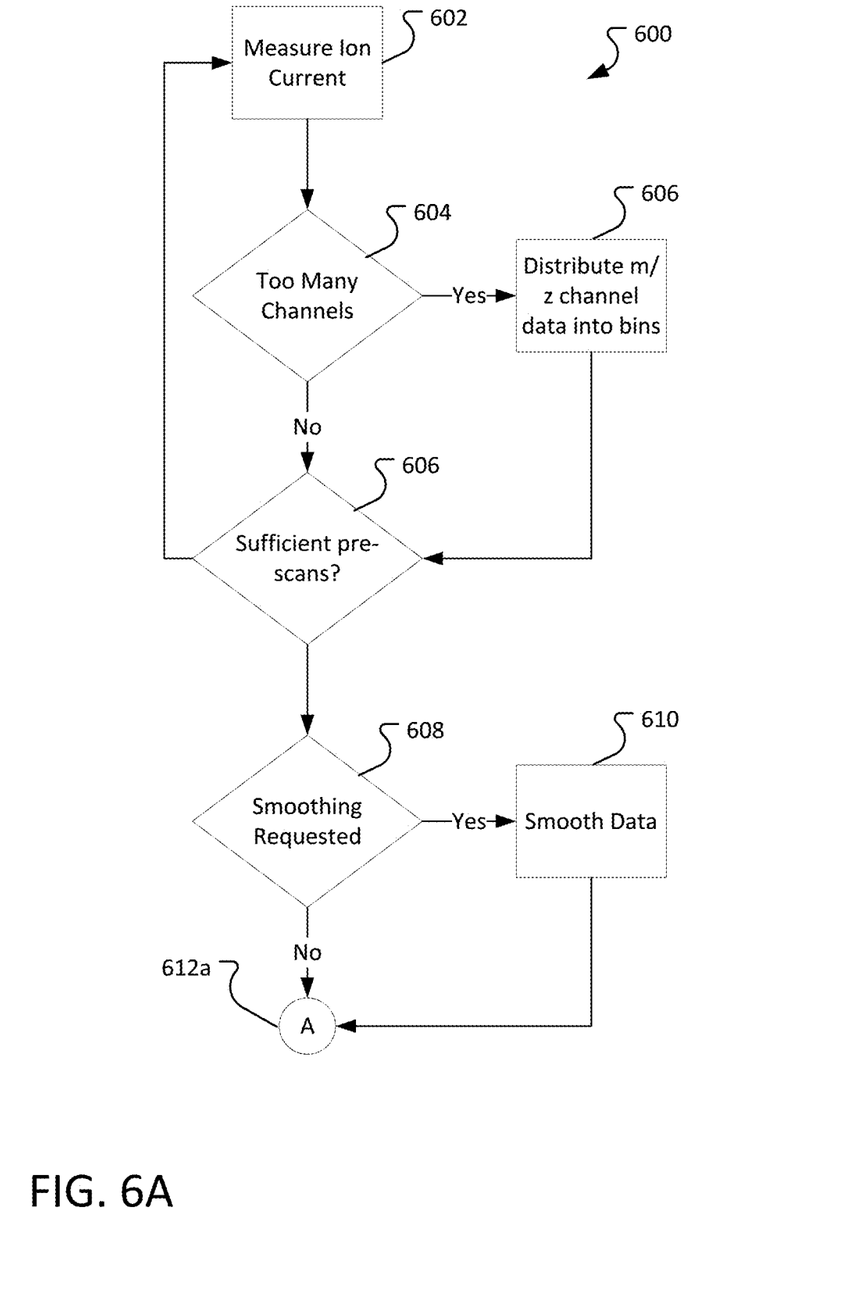
FIGS. 6A-C are a flowchart of an exemplary process for generating a control signal.
Figure 6B:
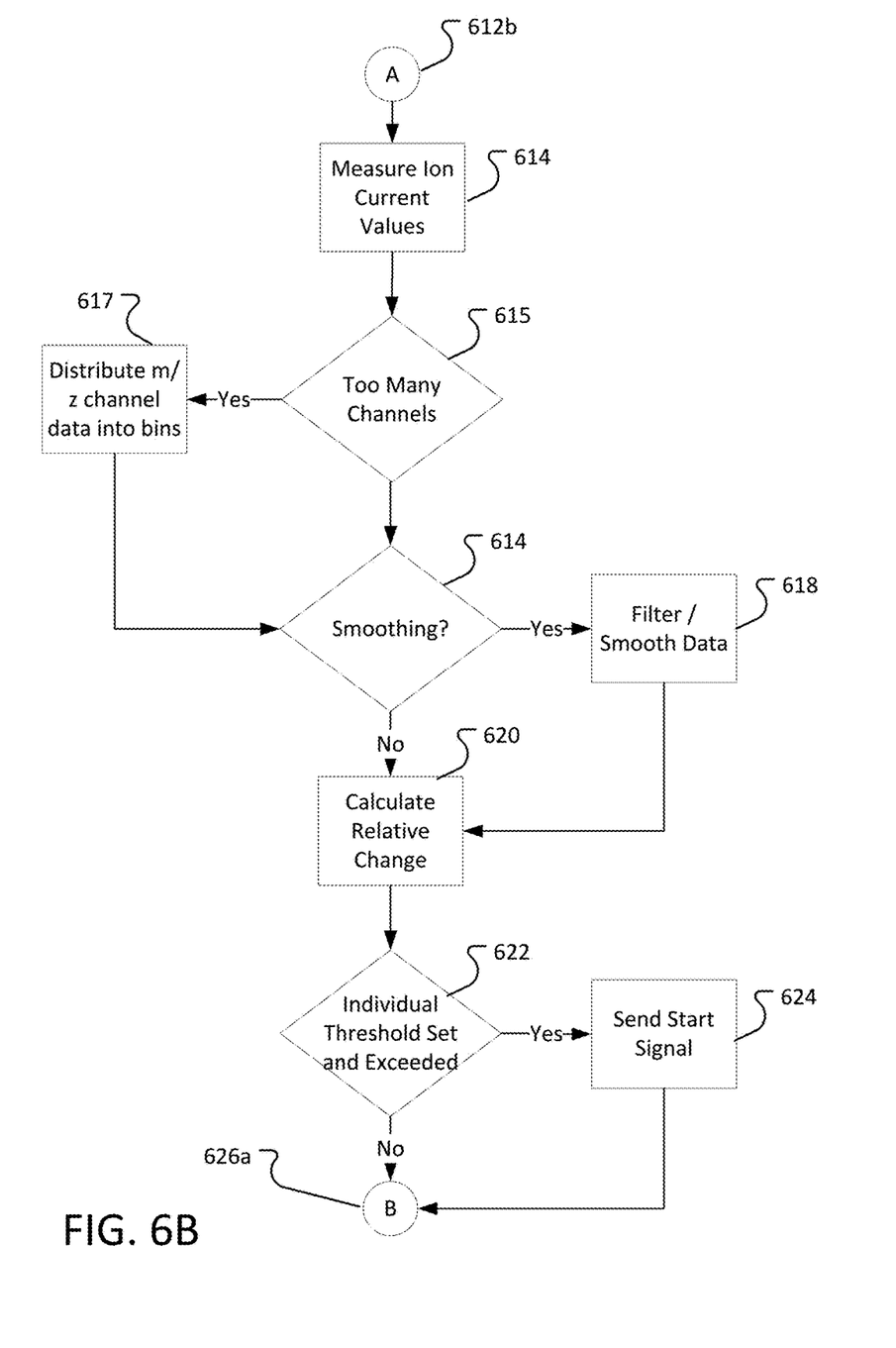
Figure 6C:
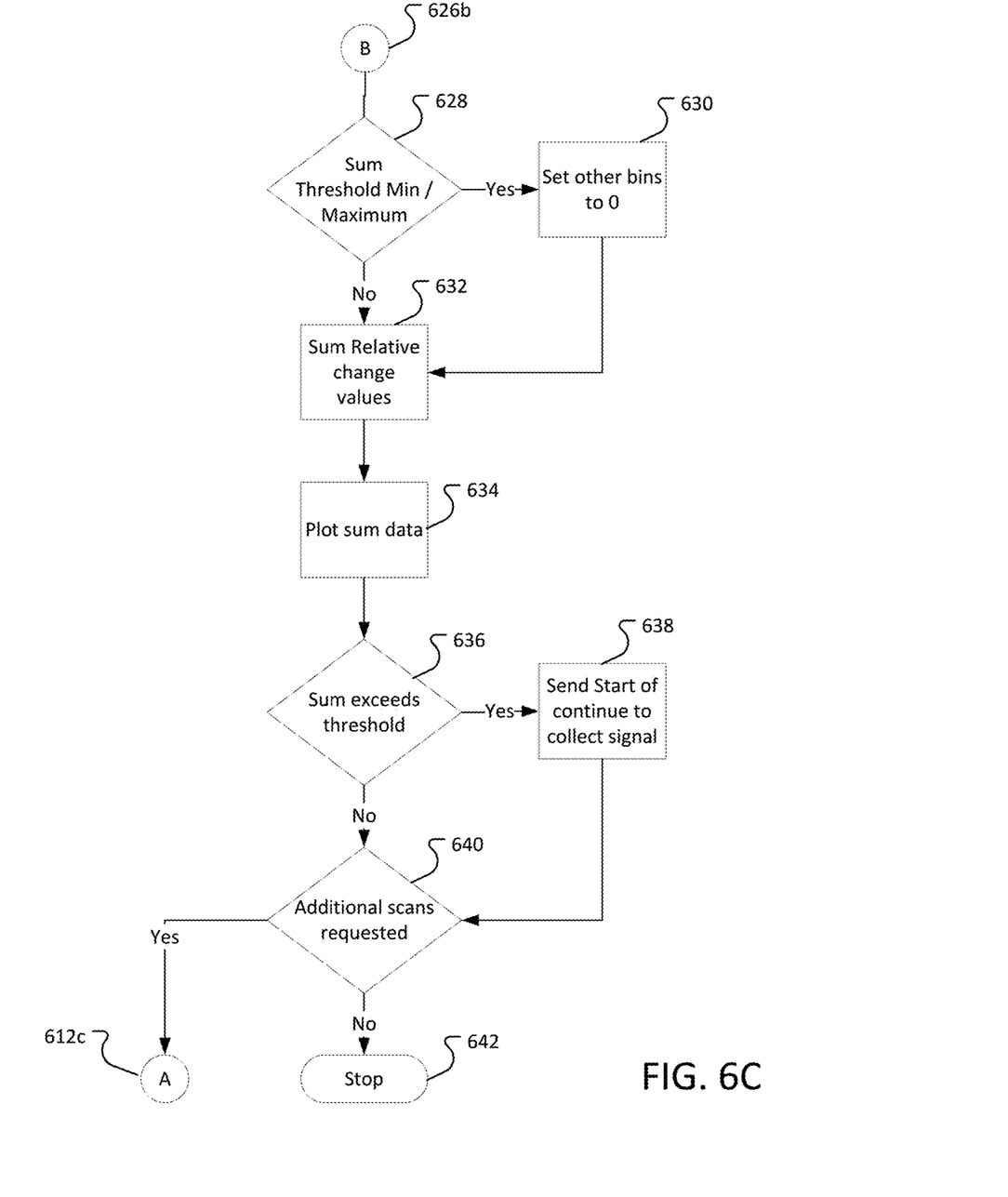

FIGS. 6A-C are a flowchart 600 of an exemplary process for generating a control signal. The process can be performed by a system that includes a mass spectrometer and a controller for processing signals from the mass spectrometer. In this example, the system includes a liquid handler in the form of a fraction collector. While described in terms of fraction collecting, it is understood, that the process may be used in other environments and may provide signals to other downstream components.

The process measures 602 the ion current. The ion current values can be measured for all m/z channels in a requested scan range.

The process determines 604 if the number of m/z channels received is greater than a threshold maximum number of intervals.

If the number of m/z channels received is greater than the threshold maximum number of intervals, the process evenly distributes 606 the m/z channel data into bins. The m/z channel data is averaged across each bin.

The process determines 606 if a sufficient number of pre-scans have been recorded. The sufficient number of pre-scans may be determined based on a threshold number of scans. If the predetermined number of pre-scans have not been recorded, the process returns to measure 602 ion current.

If a predetermined number of pre-scans have been recorded, the process determines 608 whether filtering and/or smoothing of data has been requested. If filtering and/or smoothing has been requested, then the process filters and/or smooths 610 the data across proximal m/z intervals.

The process continues with point 612a of FIG. 6A connecting to point 612b on FIG. 6B.

The process measures 614 the ion current values across all m/z intervals in the requested scan range.

The process determines 615 if the number of m/z channels received is greater than a threshold maximum number of intervals.

If the number of m/z channels received is greater than the threshold maximum number of intervals, the process evenly distributes 617 the m/z channel data into bins. The m/z channel data is averaged across each bin.

The process determines 616 whether filtering and/or smoothing of data has been requested. If filtering and/or smoothing has been requested, then the process filter and/or smooths 618 the data across the proximal m/z intervals.

The process calculates 620 the relative change of each interval from that intervals pre-scan average. In some implementations the average may be determined on a rolling basis (for example, from the last 5 current values).

The process determines 622 if there is any individual interval that exceeds a threshold (if an individual bin threshold has been set). If so, the process sends 624 a signal to start collecting a fraction.

The process continues with point 626a of FIG. 6B connecting to point 626b or FIG. 6C.

The process determines 628 if there is a minimum and/or a maximum threshold interval value to be included in the sum. If so, the process sets 630 the interval values that do not meet the criteria to 0 and/or excludes those intervals from the sum.

The process sums 632 the relative change in values of all the bins in the scan.

In some implementations, the process plots 634 the relative sim data point to the DIC vs. time graph on a user interface.

The process determines 636 if there is a relative change in sum threshold set, and if so, does the current sum exceed that threshold.

If the current sum exceeds the set threshold, the process sends 638 a signal to the fraction collector to start or continue collecting.

If process determines 640 whether there are any additional scans requested. If so the process continues with point 612c of FIG. 6C connecting to point 612b of FIG. 6B, otherwise it ends 642.

Embodiments of the subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs (i.e., one or more modules of computer program instructions, encoded on computer storage mediums for execution by, or to control the operation of, data processing apparatus). A computer storage medium can be, or be included in, a computer-readable storage device, a computer-readable storage substrate, a random or serial access memory array or device, or a combination of one or more of them. The computer storage medium can also be, or be included in, one or more separate physical components or media (e.g., multiple CDs, disks, or other storage devices). The computer storage medium can be non-transitory.

The operations described in this specification can be implemented as operations performed by a data processing apparatus on data stored on one or more computer-readable storage devices or received from other sources.

The term "data processing apparatus" encompasses all kinds of apparatus, devices, and machines for processing data, including by way of example, a programmable processor, a computer, a system on a chip, or multiple ones, or combinations, of the foregoing. The apparatus can include special purpose logic circuitry (e.g., an FPGA (field programmable gate array) or an ASIC (application-specific integrated circuit)). The apparatus can also include, in addition to hardware, code that creates an execution environment for the computer program in question (e.g., code that constitutes processor firmware, a protocol stack, a database management system, an operating system, a cross-platform runtime environment, a virtual machine, or a combination of one or more of them). The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural or object-oriented or functional languages, and it can be deployed in any form, including as a stand-alone program or as a module, component, subroutine, service, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry (e.g., an FPGA (field programmable gate array) or an ASIC (application-specific integrated circuit)).

Processors suitable for the execution of a computer program include, by way of example, both general and special purpose microprocessors, and any one or more processors of any kind of digital, analog or quantum computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive, data from or transfer data to, or both, one or more mass storage devices for storing data (e.g., electronic, magnetic, magneto-optical disks, or optical disks), however, a computer need not have such devices. Moreover, a computer can be embedded in another device (e.g., a mobile telephone, a personal digital assistant (PDA), a mobile audio or video player, a game console, a GPS receiver, or a portable storage device (e.g., a universal serial bus (USB) flash drive)), to name just a few. Devices suitable for storing computer program instructions and data include all forms of non-volatile memory, media and memory devices, including by way of example semiconductor memory devices (e.g., EPROM, EEPROM, and flash memory devices), magnetic disks (e.g., internal hard disks or removable disks), magneto-optical disks, and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback) and input from the user can be received in any form, including acoustic, speech, or tactile input. In addition, a computer can interact with a user by sending documents to and receiving documents from a device that is used by the user (for example, by sending web pages to a web browser on a user's user device in response to requests received from the web browser).

Embodiments of the subject matter described in this specification can be implemented in a computing system that includes a back-end component (e.g., as a data server), a middleware component (e.g., an application server), or a front-end component (e.g., a user computer having a graphical user interface or a Web browser through which a user can interact with an implementation of the subject matter described in this specification), or any combination of one or more such back-end, middleware, or front-end components. The components of the system can be interconnected by any form or medium of digital or optical data communication (e.g., a communication network). Examples of communication networks include a local area network ("LAN") and a wide area network ("WAN"), an inter-network (e.g., the Internet), and peer-to-peer networks (e.g., ad hoc peer-to-peer networks).

The computing system can include users and servers. A user and server are generally remote from each other and typically interact through a communication network. The relationship of user and server arises by virtue of computer programs running on the respective computers and having a user-server relationship to each other. In some embodiments, a server transmits data (e.g., an HTML page) to a user device (e.g., for purposes of displaying data to and receiving user input from a user interacting with the user device). Data generated at the user device (e.g., a result of the user interaction) can be received from the user device at the server.

While this specification contains many specific implementation details, these should not be construed as limitations on the scope of any inventions or of what may be claimed, but rather as descriptions of features specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can, in some cases, be excised from the combination, and the claimed combination may be directed to a sub combination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. A system comprising:
   a mass spectrometer, the mass spectrometer providing ion current measurement for a plurality of mass to charge channels over a period of time;
   a controller coupled to the mass spectrometer; and
   a liquid handler coupled to the controller and the mass spectrometer;
   wherein the controller is configured to:
   identify a base average ion current of each mass to charge interval, the mass to charge interval comprising at least one mass to charge channel;

calculate a relative change between a current ion current measurement for a charge interval to the base average for the charge interval;

calculate a sum of the relative changes for each charge interval in the scan;

compare the sum of relative changes to a threshold; and in response to determining that the sum of relative changes exceeds the threshold, start fraction collection using the liquid handler.

2. The system of claim 1, wherein the controller is further configured to plot the sum relative changes for each charge interval of a scan vs the time of the scan.

3. The system of claim 1, wherein the mass to charge interval includes a plurality of mass to charge channels.

4. The system of claim 1, wherein the base average is determined based on one or more prior scans of a sample at a fixed time.

5. The system of claim 1, wherein the base average is determined on a rolling basis based on received information about one or more prior scans of a sample at a fixed time difference from the current scan.

6. The system of claim 5, wherein the controller is further configured to stop fraction collection in response to at least one of a fixed time, an indication by a rolling relative change to go to a next vial, a fixed relative change, and an extracted ion current determined by an algorithm of the rolling relative change.

7. The system of claim 1, wherein the controller is further configured to apply algorithmic smoothing to the ion current measurements in a scan of mass to charge channels.

8. The system of claim 1, wherein the controller is further configured to apply algorithmic smoothing to the relative changes in a scan of mass to charge channels.

9. A method for controlling a liquid handler comprising:

receiving ion current measurements for a plurality of mass to charge channels over a period of time from a mass spectrometer;

identifying a base average ion current of each mass to charge interval, the mass to charge interval comprising at least one mass to charge channel;

calculating a relative change between a current ion current measurement for a charge interval to the base average for the charge interval;

calculating a sum of the relative changes for each charge interval in the scan;

comparing the sum of relative changes to a threshold; and in response to determining that the sum of the relative change exceeds the threshold, starting fraction collection using the liquid handler.

10. The method of claim 9, further comprising plotting the sum relative changes for each charge interval of a scan vs the time of the scan.

11. The method of claim 9, wherein the mass to charge interval includes a plurality of mass to charge channels.

12. The method of claim 9, wherein the base average is determined based on one or more prior scans of a sample at a fixed time.

13. The method of claim 9, wherein the base average is determined on a rolling basis based on received information about one or more prior scans of a sample at a fixed time difference from the current scan.

14. The method of claim 9, further comprising determining to stop fraction collection in response to at least one of a fixed time, an indication by a rolling relative change to go to a next vial, a fixed relative change, and an extracted ion current determined by an algorithm of the rolling relative change.

\* \* \* \* \*